United States Patent
Dalal et al.

(10) Patent No.: US 8,129,266 B2
(45) Date of Patent: Mar. 6, 2012

(54) METHOD OF FORMING A SHIELDED SEMICONDUCTOR DEVICE AND STRUCTURE THEREFOR

(75) Inventors: Hormazdyar M. Dalal, Lagrangeville, NY (US); Jagdish Prasad, Pocatello, ID (US)

(73) Assignee: Semiconductor Componenets Industries, LLC, Phoenix, AZ (US)

( * ) Notice: Subject to any disclaimer, the term of this patent is extended or adjusted under 35 U.S.C. 154(b) by 343 days.

(21) Appl. No.: 12/170,202

(22) Filed: Jul. 9, 2008

(65) Prior Publication Data

US 2010/0006989 A1 Jan. 14, 2010

(51) Int. Cl.
*H01L 23/552* (2006.01)
*H01L 21/768* (2006.01)

(52) U.S. Cl. ............... 438/622; 257/659; 257/E23.114; 257/E21.575

(58) Field of Classification Search ............ 257/659; 438/622

See application file for complete search history.

(56) References Cited

U.S. PATENT DOCUMENTS

| | | | |
|---|---|---|---|
| 4,933,743 A | 6/1990 | Thomas et al. | |
| 5,482,897 A | 1/1996 | Lynch | |
| 6,686,649 B1 * | 2/2004 | Mathews et al. | 257/659 |
| 6,713,317 B2 * | 3/2004 | Knapp et al. | 438/106 |
| 6,888,063 B1 | 5/2005 | Lien et al. | |
| 6,953,698 B2 * | 10/2005 | Casey et al. | 438/15 |
| 7,187,060 B2 * | 3/2007 | Usui | 257/659 |
| 2003/0052352 A1 * | 3/2003 | Soeda | 257/296 |
| 2004/0029312 A1 * | 2/2004 | Knapp et al. | 438/106 |
| 2005/0253223 A1 * | 11/2005 | Marques | 257/659 |
| 2007/0194427 A1 * | 8/2007 | Choi et al. | 257/686 |
| 2009/0020856 A1 * | 1/2009 | Collins et al. | 257/665 |
| 2009/0106713 A1 * | 4/2009 | Collins et al. | 716/4 |
| 2009/0302438 A1 * | 12/2009 | Chauhan et al. | 257/659 |

FOREIGN PATENT DOCUMENTS

JP 2007-263681 A 10/2007

* cited by examiner

*Primary Examiner* — N Drew Richards
*Assistant Examiner* — Robert Carpenter
(74) *Attorney, Agent, or Firm* — Robert F. Hightower (57) ABSTRACT

In one embodiment, a semiconductor device is formed to include a plurality of conductor layers that interconnect electrical signals between semiconductor elements of the semiconductor device. A metal shield layer is formed overlying a portion of the plurality of conductor layers. A signal redistribution layer is formed overlying the metal shield layer.

11 Claims, 7 Drawing Sheets

METHOD OF FORMING A SHIELDED SEMICONDUCTOR DEVICE AND STRUCTURE THEREFOR

BACKGROUND OF THE INVENTION

The present invention relates, in general, to electronics, and more particularly, to semiconductors, structures thereof, and methods of forming semiconductor devices.

In the past, the semiconductor industry utilized various methods and structures to form medical semiconductor devices that were attached to or implanted within a medical patient to assist with various medical needs of the patient. One example of such a medical device was an implantable Cardioverter-defibrillator device that could monitor heart rhythms and provide a defibrillation function in the event of abnormal heart activity. The medical devices generally were hermetically sealed within a metal casing such as a titanium casing. In order to remotely monitor any data that was stored within the medical device, an antenna was provided on the outside of the metal casing which allowed wireless communication between the medical device and another wireless device such as a cellular phone.

The external antenna required feed-throughs in the metal casing and sealing thereof which increased the cost of the resulting encased medical device. Additionally, the external antenna made the medical device large and bulky which made implantation more difficult and expensive.

Accordingly, it is desirable to have a medical device that has a lower cost, and that has a smaller form factor for implantation.

For simplicity and clarity of the illustration, elements in the figures are not necessarily to scale, and the same reference numbers in different figures denote the same elements. Additionally, descriptions and details of well-known steps and elements are omitted for simplicity of the description. As used herein current carrying electrode means an element of a device that carries current through the device such as a source or a drain of an MOS transistor or an emitter or a collector of a bipolar transistor or a cathode or anode of a diode, and a control electrode means an element of the device that controls current through the device such as a gate of an MOS transistor or a base of a bipolar transistor. Although the devices are explained herein as certain N-channel or P-Channel devices, or certain N-type or P-type doped regions, a person of ordinary skill in the art will appreciate that complementary devices are also possible in accordance with the present invention. It will be appreciated by those skilled in the art that the words during, while, and when as used herein relating to circuit operation are not exact terms that mean an action takes place instantly upon an initiating action but that there may be some small but reasonable delay, such as a propagation delay, between the reaction that is initiated by the initial action. The use of the word approximately or substantially means that a value of an element has a parameter that is expected to be very close to a stated value or position. However, as is well known in the art there are always minor variances that prevent the values or positions from being exactly as stated. It is well established in the art that variances of up to at least ten percent (10%) (and up to twenty percent (20%) for semiconductor doping concentrations) are reasonable variances from the ideal goal of exactly as described. For clarity of the drawings, doped regions of device structures are illustrated as having generally straight line edges and precise angular corners. However, those skilled in the art understand that due to the diffusion and activation of dopants the edges of doped regions generally may not be straight lines and the corners may not be precise angles.

DETAILED DESCRIPTION OF THE DRAWINGS

Figure 1:
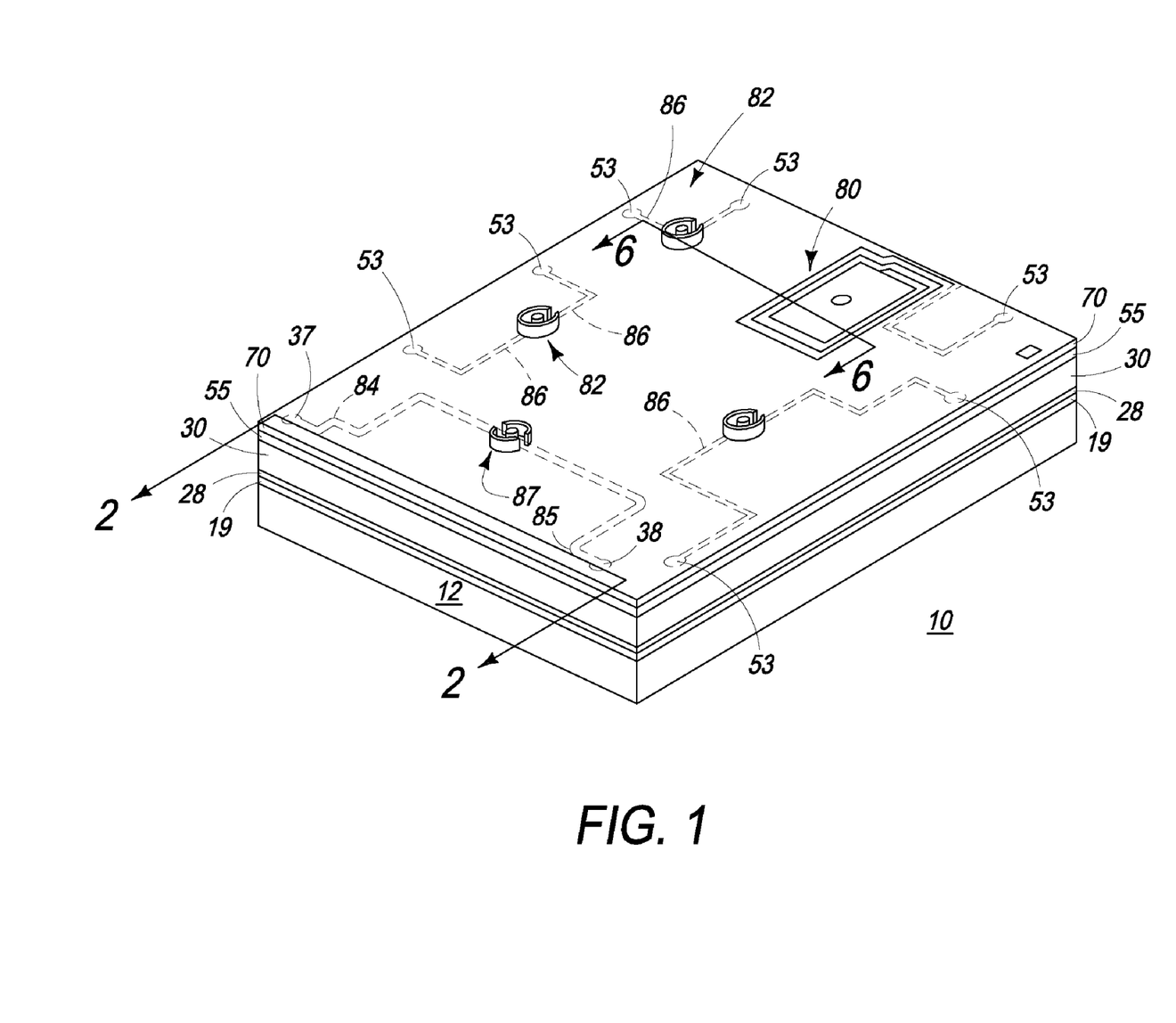
FIG. 1 illustrates an enlarged isometric view of a portion of a preferred embodiment of a medical semiconductor device in accordance with the present invention.

FIG. 1 illustrates an enlarged isometric view of a portion of a preferred embodiment of a medical semiconductor device 10 that is formed on a semiconductor substrate 12. Device 10 is formed with a signal re-distribution layer that includes an antenna 80 which may be used to provide wireless communication between device 10 and an external wireless device such as a cellular phone. The signal re-distribution layer of device 10 also includes coaxial connector bases 82 and 87 that facilitate connecting device 10 to external electronic equipment through coaxial cables that may be attached to coaxial connector bases 82 and 87. One of bases 82 usually is connected to a source of power and a common reference, such as a ground reference, for operating device 10. Some of bases 82 and 87 are connected to underlying semiconductor devices of device 10 through conductors of the signal re-distribution layer such as conductors 84, 85, and 86. Some of conductors 84, 85, and 86 are illustrated in dashed lines to represent that the conductors may be covered and may not be directly seen from the illustrated view. As will be seen further hereinafter, device 10 includes a plurality of interconnect layers having inter-layer conductors that are formed between inter-layer dielectrics, such as an inter-layer dielectric 19 and an inter-layer dielectric 28. A last inter-layer conductor of the plurality of interconnect layers usually is formed on an inter-layer dielectric but usually is covered by a passivation layer instead of an inter-layer dielectric. Additionally, a metal shield layer (not shown in FIG. 1) is formed between the signal re-distribution layer and the plurality of interconnect layers.

Figure 2:
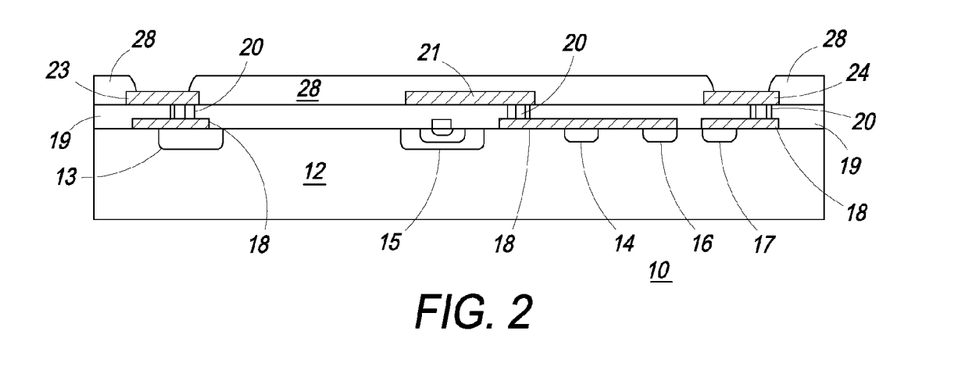
FIG. 2 illustrates an enlarged cross-sectional view of a portion of the preferred embodiment of the medical semiconductor device of FIG. 1 at a stage in a preferred embodiment of a process for forming the medical semiconductor device in accordance with the present invention.

FIG. 2 illustrates an enlarged cross-sectional view of a portion of the preferred embodiment of device 10 at a stage in a preferred embodiment of a process for forming device 10. The cross-sectional view is illustrated along cross-section line 2-2 of FIG. 1. Device 10 is formed on semiconductor substrate 12. A plurality of semiconductor devices typically is formed on the surface substrate 12 in order to provide the functional characteristics that are desired for device 10. The plurality of semiconductor devices may include a plurality of active and passive semiconductor devices such as transistors, diodes, resistors, capacitors, or charge retention cells. For example, device 10 may include bipolar transistors illustrated by a bipolar transistor 15 or MOS transistors such as MOS transistors 14 and 16. Device 10 may also include diodes such as a diode 13 or passive semiconductor devices such as a resistor 17. These semiconductor devices usually are interconnected through the inter-layer conductors of the interconnect layers to form electrical circuits to provide digital functions, analog functions, sensing, filtering, data storage functions, and other functions required in a particular application for device 10. After forming the semiconductor elements or devices on substrate 12, a first inter-layer dielectric (not shown) usually is applied to the surface of substrate 12 and patterned to form openings where it is desired to make electrical connections to the underlying semiconductor devices such as transistors 14-16. A first inter-layer conductor is formed in the first inter-layer dielectric to electrically connect some of the desired semiconductor devices. Typically, a conductor material is applied and then patterned to form the inter-layer conductors, such as conductors 18. The inter-layer conductors are used to conduct electrical signals that are formed by the semiconductor elements of device 10. Some of the inter-layer conductors may also provide power and ground to the semiconductor devices. A second inter-layer conductor may be utilized to provide additional electrical interconnects and conduct additional electrical signals between the semiconductor devices. A second inter-layer dielectric 19 usually is formed on the first inter-layer conductors. Openings or vias 20 are formed through dielectric 19 to electrically contact the desired portions of the first inter-layer conductors, such as conductors 18. Thereafter conductor layer is formed on dielectric 19 to form conductors that conduct electrical signals such as conductors 21, 23, and 24. Usually conductors 21, 23, and 24 are formed by applying a conductor material and patterning the conductor material into the desired conductors 21, 23, and 24. Thereafter, an inter-layer dielectric 28 is formed overlying conductors 21, 23, and 24. Openings are formed through dielectric 28 in areas where it is desired to make electrical connection to portions of the second inter-layer conductor. In some embodiments, dielectric 28 is the final dielectric layer, thus, dielectric 28 is formed as a passivation layer that is used to protect device 10 from the external environment. Such a passivation layer usually includes silicon nitride in order to make dielectric 28 impervious to contaminants that could react with the materials of device 10 and cause the active semiconductor elements to fail. In some cases, the passivation layer may also include polyimide, spin-on glass, or combinations thereof. For clarity of the drawings, only one conductor 21 is illustrated in FIG. 2, however, those skilled in the art will appreciate that the second inter-layer conductor usually includes many different conductors. Those skilled in the art will also appreciate that the power and ground signals generally are routed to the semiconductor device on the inter-layer conductors.

Figure 3:
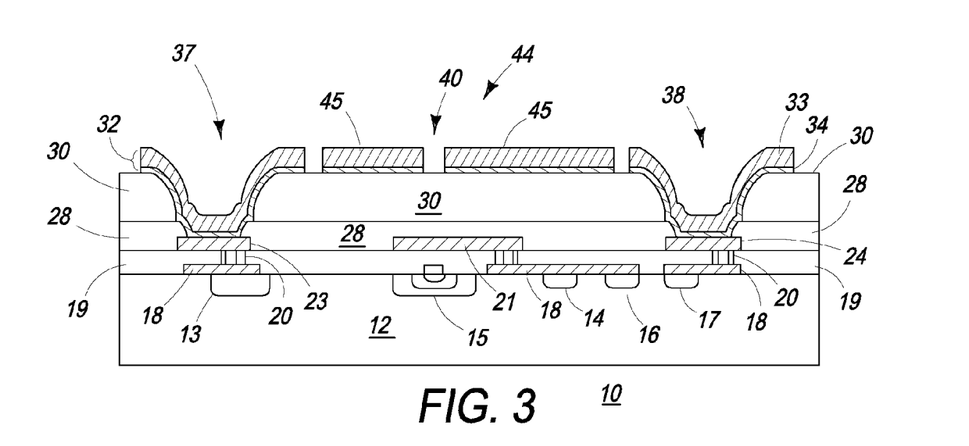
FIG. 3 illustrates the medical semiconductor device of FIG. 2 at a subsequent stage of the process in accordance with the present invention.

FIG. 3 illustrates a subsequent stage in the preferred embodiment of the process for forming device 10. A dielectric layer 30 is formed overlying dielectrics 19 and 28 and overlying conductors 18 and 21. Openings are formed through dielectric layer 30 in areas where it is desired to make electrical connection to the inter-layer conductors such as conductors 21, 23, and 24. The material used for forming dielectric layer 30 may be any of a variety of well-known dielectric materials such as silicon dioxide, silicon nitride, organo-silicate glass (SOG), or other silicon containing dielectrics. Flowable and photo-imageable organic dielectrics are preferred because they usually have a lower dielectric constant and lower cost, because they generally can be formed into a thick layer, and because they provide a planarizing effect. Examples of such organic dielectrics include polyamides and Benzocyclo Butanes (BCB).

Thereafter, a metal shield layer 44 is formed preferably on the surface of layer 30 and overlying at least a portion of the inter-layer conductors and overlying at least a portion of the active devices formed on substrate 12. Metal shield layer 44 is highlighted in a general manner by an arrow.

Figure 4:
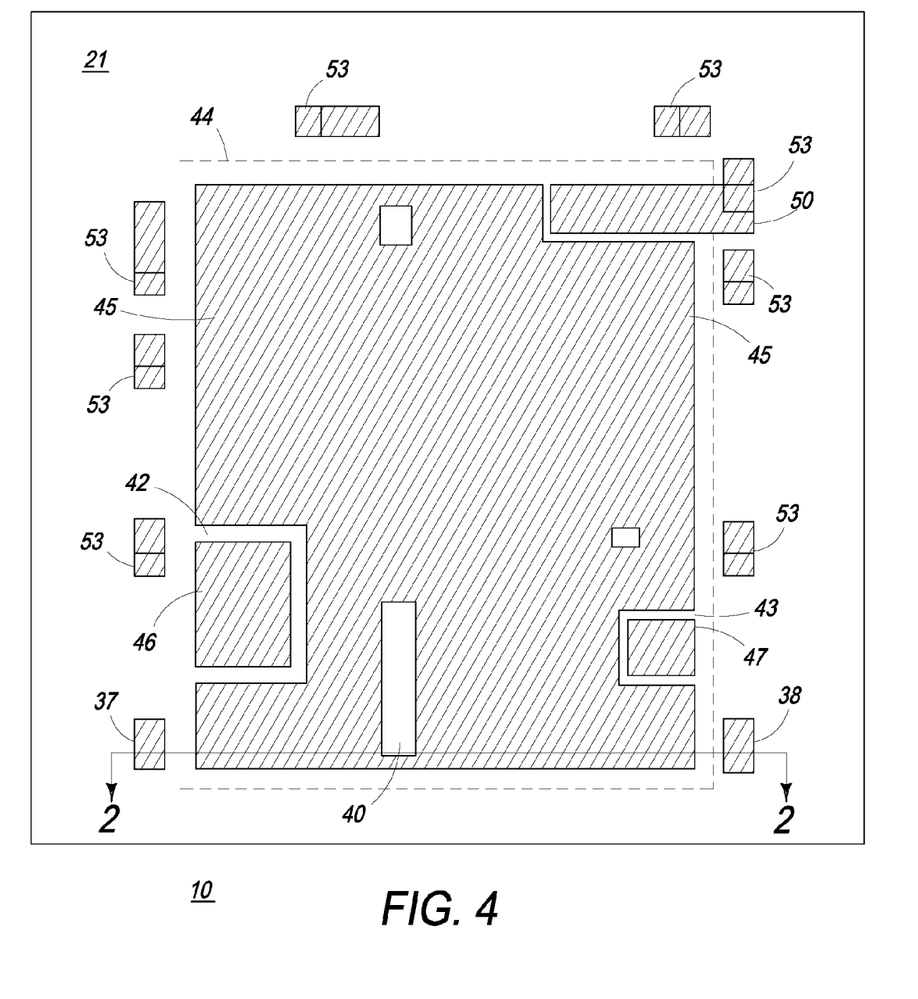
FIG. 4 illustrates an enlarged plan view of the medical semiconductor device of FIG. 3 subsequent to forming a metal shield layer in accordance with the present invention.

FIG. 4 illustrates an enlarged plan view of device 10 subsequent to forming metal shield layer 44. This description has references to FIG. 3 and FIG. 4. Cross-section line 2-2 represents the view of the cross-sections of FIG. 2 and FIG. 3. Metal shield layer 44 is identified in FIG. 4 by a dashed box. In the preferred embodiment, a metal layer 32 (FIG. 3) is blanket deposited and patterned to form metal shield layer 44. Optionally, metal layer 32 may be formed within the vias or openings of dielectric layer 30, such as vias 37 and 38, in order to facilitate subsequently forming electrical contact to conductors that are exposed by the vias, such as conductors 23 and 24. The material used for metal layer 32, thus metal shield layer 44, usually is chosen to be one of a variety of different metals that is compatible with the semiconductor processing steps used to form device 10. Examples of suitable materials usually includes aluminum, copper, an aluminum-copper alloy, gold, nickel, titanium, chromium, titanium-tungsten, or any of a variety of other well-known metals or metal alloys that are used in semiconductor processing. Metal layer 32 preferably is a multi-layer metal that includes a layer of titanium 34 that is covered by a layer of copper 33. Metal layer 32 may also be a multi-layer metal of aluminum that is covered with a layer of nickel which is covered with a layer of copper. The thickness of metal layer 32 should be sufficient to form a very low resistance electrical conductor and generally is about one to five (1-5) microns thick.

Layer 30 usually is patterned to form openings through layer 30 for vias such as vias 37, 38, and 53 (FIG. 1) that are used to provide an electrical connection through layer 30 to conductors 86 and antenna 80 (FIG. 1).

Figure 5:
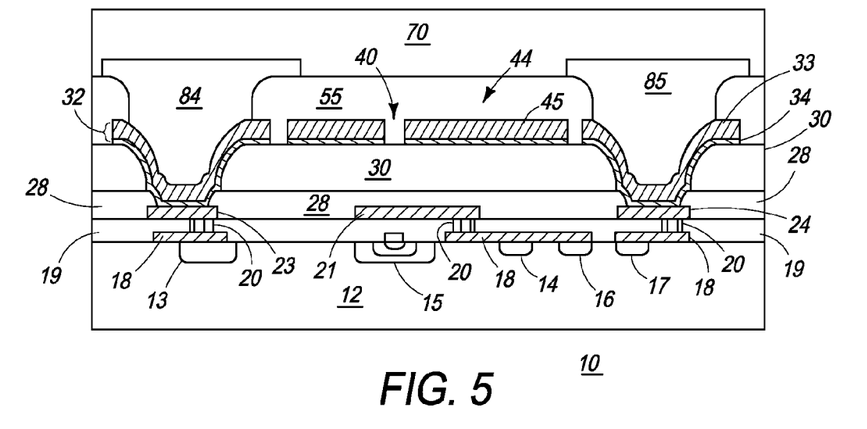
FIG. 5 illustrates the medical semiconductor device of FIG. 1 at another subsequent step in the preferred embodiment of the process in accordance with the present invention.

FIG. 5 illustrates device 10 at another subsequent step in the preferred embodiment of the process for forming device 10. This description has references to FIG. 5 and FIG. 1. Subsequent to forming metal shield layer 44, the signal redistribution layer (RDL) that includes conductors 84, 85, and 86 is formed overlying metal shield layer 44. Conductors 84, 85, and 86 (FIG. 1) are electrically connected to portions of the underlying interconnect layers, such as through vias 37, 38, and 53, thereby re-distributing electrical signals from the underlying inter-layer conductors, such as conductors 21, 23, and 24, to conductors 84, 85, and 86 that overlie metal shield layer 44. In order to facilitate forming the signal re-distribution layer, a dielectric layer 55 is formed to overlie, and preferably is formed on, metal shield layer 44. Layer 55 usually is also formed on the portions of metal layer 32 that are in the vias of device 10. The material used for layer 55 generally is similar to the material used for dielectric 30. Dielectric layer 55 is patterned to form openings through dielectric layer 55 where it is desired to connect to the underlying inter-layer conductors. Thereafter, a conductor material is formed in the openings to make an electrical connection to the inter-layer conductors and vias. The connections to the underlying inter-layer conductors usually are made around the outside edges of device 10 as illustrated by vias 53 in FIG. 1. FIG. 4 also illustrates these connections. The conductor material is used to form conductors 84, 85, and 86 extending across layer 55 in order to rout the signals from the underlying inter-layer conductors to the desired positions on the top surface of device 10. The conductor material may also be used to form coaxial connector bases 82 and 87 and antenna 80 (FIG. 1). The conductor material preferably is applied by using electroplating plating techniques with a metal or metal alloy. Other metal deposition techniques that are well known to those skilled in the art may also be used. Alternately, the material used for antenna may be copper, gold, or alloys thereof, or an iron alloy. Thereafter, another dielectric layer 70 is deposited over the conductors of the re-distribution layer. The material used for layer 70 usually is chosen from the same type of materials as layer 30. Openings are formed in layer 70 overlying antenna 80 and bases 82 and 87 to allow physical access thereto.

Referring to FIG. 4 in addition to FIG. 1 and FIG. 5, metal shield layer 44 usually includes a plurality of metal regions such as metal regions 45, 46, 47, and 50. Those skilled in the art will appreciate that during the operation of device 10, the signals that are coupled to conductors 84, 85, and 86 (FIG. 1) may generate electro-magnetic interference (EMI) that could interfere with the operation of some of the underlying semiconductor elements such as analog circuits and related analog semiconductor devices. Each of metal regions 45, 46, 47, and 50 typically are formed to overlie regions of device 10 wherein the operation of the underlying semiconductor elements may undesirably be affected by such EMI. For example, metal region 45 may be formed overlying analog circuitry that is configured to monitor blood pressure or the heart rate of a patient. Coupling EMI from conductors 84, 85, and 86 into the sensitive analog circuitry could affect the accuracy of the measurements of the analog circuitry. Metal regions 45, 46, 47, and 50 terminate some of the electro-magnetic interference (EMI) thereby reducing the noise coupled into the underlying semiconductor devices. Metal shield layer 44 also reduces coupling between the various semiconductor elements during the operation of device 10. For example, metal region 46 may overlie digital circuitry that is operating at a high high-speed. In such an embodiment, metal region 46 could terminate some of the EMI from such circuits and reduce the noise that could be coupled into other semiconductor devices of device 10. In such an embodiment, separating region 46 from regions 45, 47, and 50 assists in isolating the signals to region 46 and prevents radiating the noise to regions 45, 47, and 50. In some instances, it may be desirable to form an opening within a portion of one of the metal regions overlying semiconductor elements or devices that generate high-frequency signals with a large number of harmonics. These openings, such as an opening 40 through metal region 45 above bipolar transistor 15, minimize coupling of the harmonics into the metal region, such as metal region 45, which in turn reduces coupling of these harmonics to other sensitive elements of device 10. In some embodiments, it may be desirable to provide slits within metal shield layer 44 to block the propagation of radio-frequency (RF) energy, such as from antenna 80 (FIG. 1), into the semiconductor elements underlying the metal regions of metal shield layer 44. For example, slit 42 may prevent energy that is coupled into metal region 46 from being propagated into metal region 45. The width and length of the slits usually are determined by the frequency that is to be blocked in addition to the capacitance and inductance of the inter-layer conductors underlying layer 44. In some embodiments, it may be desirable for metal shield layer 44 to have only one metal region instead of the plurality of metal regions illustrated in FIG. 4. All of the regions of layer 44 may be connected to the same potential or may be left floating. Some or all regions of metal shield layer 44 may electrically float and not be connected to a specific electrical potential. Other regions or all regions may be connected to a common system reference, such as system ground potential. The ground potential can assist in preventing corrosion of layer 44. In some cases, some or all regions of layer 44 may be connected to a positive bias voltage or even to the potential of the operating power supply voltage. The positive potential may assist in repelling alpha particles. Those skilled in the art will appreciate that even though layer 44 or portions thereof may connected to a potential or common reference, those portions of layer 44 do not distribute such potentials to the devices of device 10, thus, layer 44 is not connected in series between the source of the potential and any of the devices, such as devices 13-17, of device 10. Layer 44 usually is not physically connected to any of the devices of device 10. Additionally, the width of layer 44 and any portions thereof usually is greater than the width of any of the inter-layer conductors or of the power distribution conductors of device 10.

The thickness of dielectric layer 30 is chosen to provide a distance between metal shield layer 44 and the underlying interconnect layers, such as the distance to inter-layer conductor 21, that is sufficient to reduce electrical coupling of signals within layer 44 to the underlying interconnect layers. Generally, the thickness of dielectric layer 30 is about two to fifteen (2-15) microns and preferably is about six microns. In contrast, the thickness of inter-layer dielectrics 19 and 28 generally is about one to five (1-5) microns.

Figure 6:
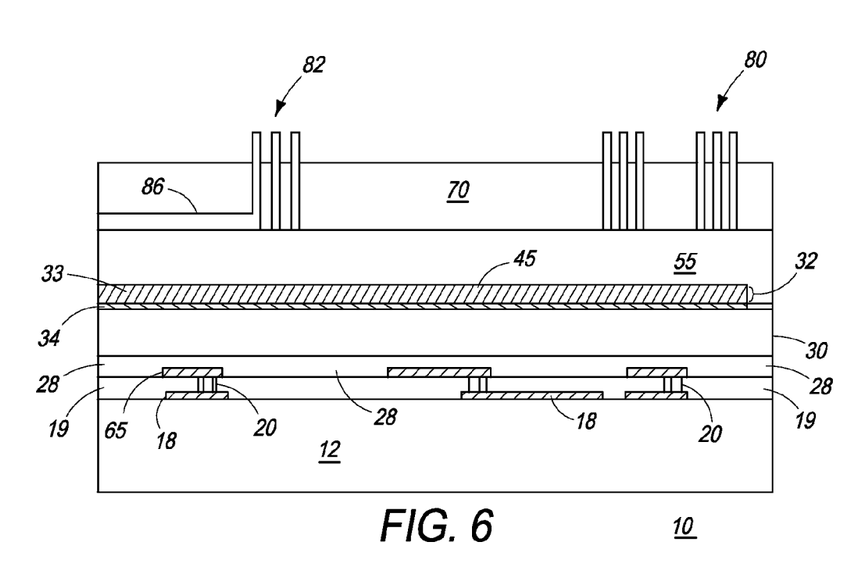
FIG. 6 illustrates an alternate embodiment of the medical semiconductor device of FIG. 5 in accordance with the present invention.

FIG. 6 illustrates an alternate embodiment of device 10 wherein antenna 80 and bases 82 are formed to extend above the surface of dielectric layer 70. In order to extend the height of antenna 80 and bases 82, repeated electro-plating steps may be performed to increase the thickness of the conductor material used to form antenna 80 and bases 82.

Figure 7:
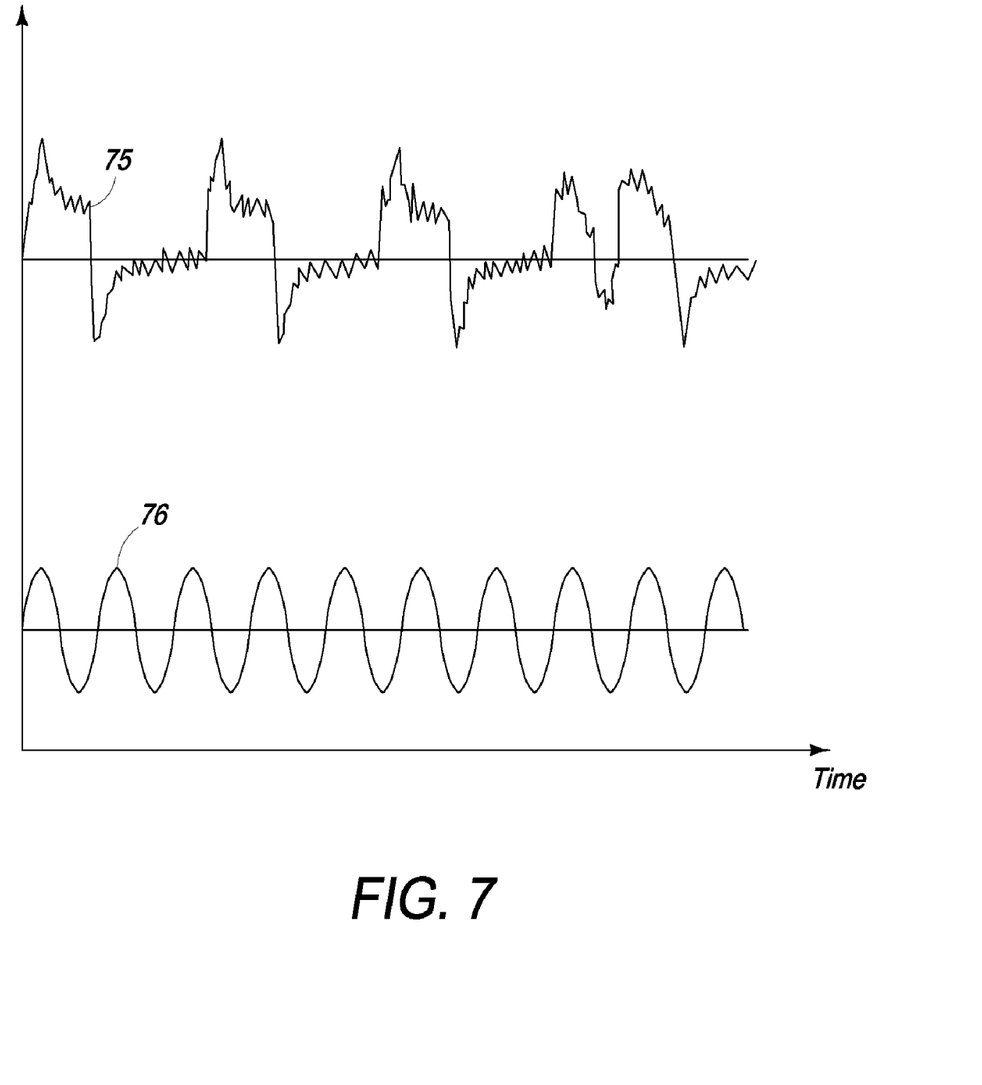
FIG. 7 is a graph having plots that illustrate a signal of the medical semiconductor device of FIG. 1 in accordance with the present invention.

FIG. 7 is a graph having plots that illustrate a comparison of signals from device 10 to a device that does not have metal shield layer 44. The abscissa indicates time and the ordinate indicates increasing value of the illustrated signal. A plot 76 illustrates a signal formed by one of the semiconductor devices of device 10 during the operation of device 10. The signal illustrated in plot 76 is taken on one of the inter-layer conductors of device 10 and not on the signal re-distribution layer. A plot 75 illustrates a signal formed by a medical semiconductor device that is similar to device 10 except that it does not have metal shield layer 44. Plot 75 has a large number of noise spikes distributed through the waveform of the signal illustrated by plot 75. As can be seen from plot 76, metal shield layer 44 has substantially protected signal 76 from any noise that may be generated during the operation of device 10.

Figure 8:
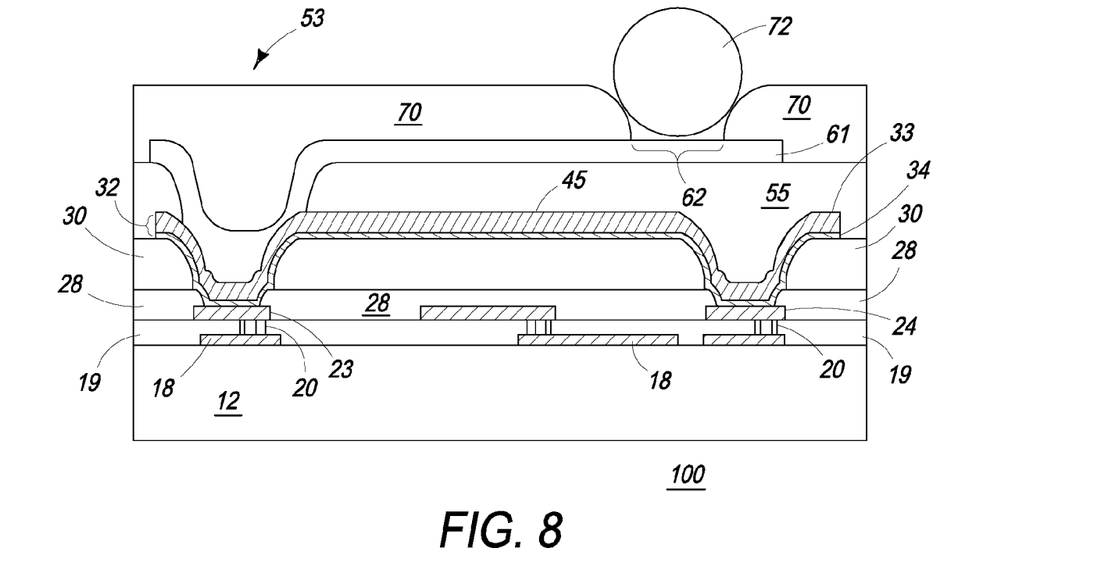
FIG. 8 illustrates an enlarged cross-sectional view of a portion of an alternate embodiment of the medical semiconductor device of FIG. 1 in accordance with the present invention.

FIG. 8 illustrates an enlarged cross-sectional view of a portion of a medical semiconductor device 100 that is an alternate embodiment of device 10. Device 100 is similar to device 10 except that re-distribution layer of device 100 is used for a ball grid array connector arrangement instead of antenna 80 and coax bases 82 and 87. For such a ball grid array embodiment, openings may be formed in layer 55 overlying portions of the inter-layer conductors that are to be used to provide signals on the re-distribution layer. For example, an opening may be formed in layer 55 overlying conductor 23. Such openings generally are formed along the outside perimeter of device 10 as illustrated by vias 53 in FIG. 9. A conductor 61 may be applied to contact conductor 23. Conductor 61 is formed to extend across layer 55 to rout or re-distribute the signal from conductor 23 to a point where it is easier to make electrical contact and gain access to the appropriate electrical signal. Thereafter, dielectric layer 70 is applied and patterned to form openings where physical contact will be made to conductor 61 thereby making electrical contact to conductor 23. Typically, a solder ball 72 is formed within the opening to make electrical connection to conductor 23. A portion of conductor 61 may form a bump pad 62 where ball 72 is positioned. Thus, the electrical signal from conductor 23 has been re-distributed across the top surface of device 10.

Figure 9:
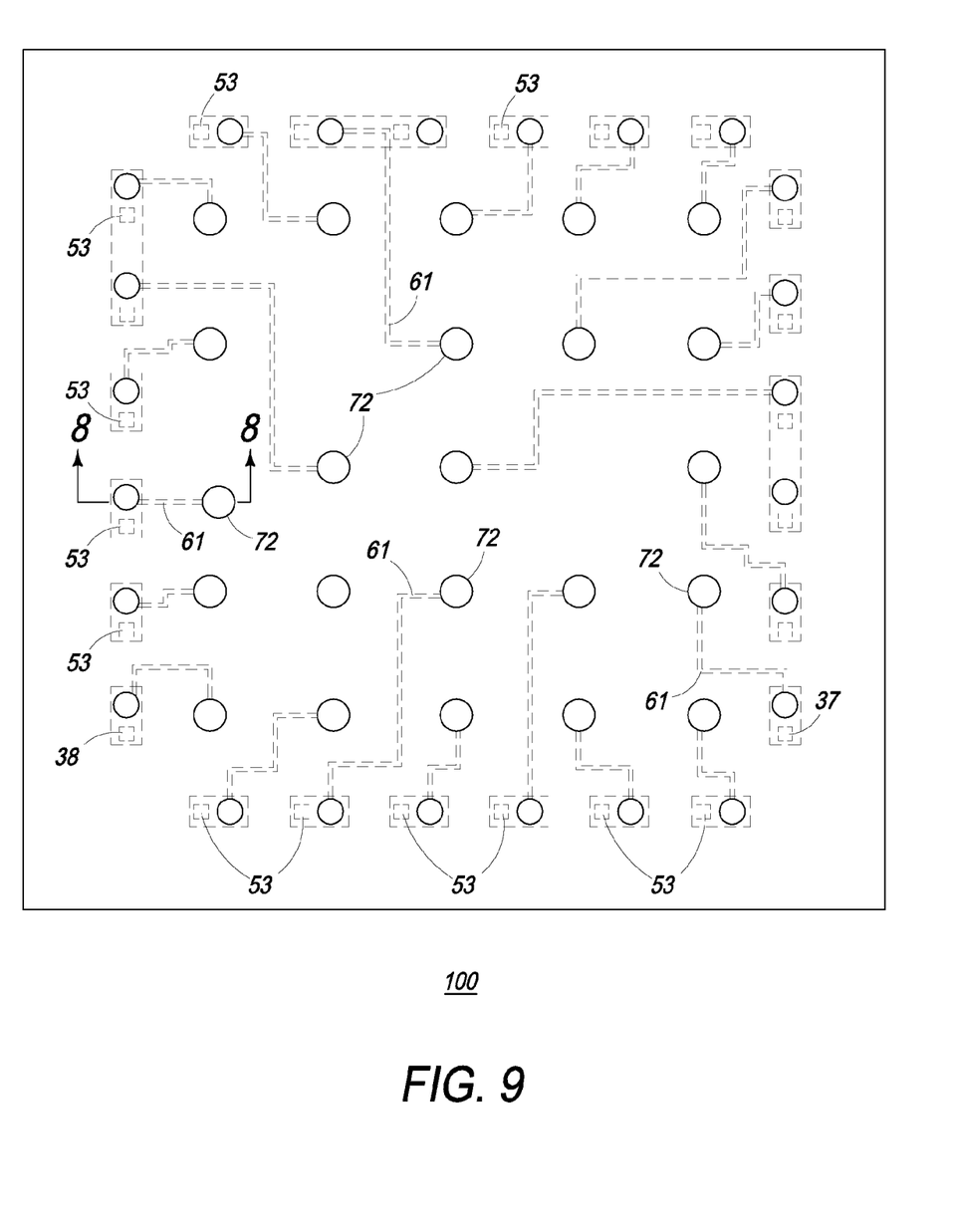
FIG. 9 illustrates an enlarged plan view of a portion of the medical semiconductor device of FIG. 8 in accordance with the present invention.

FIG. 9 illustrates an enlarged plan view of a portion of medical semiconductor device 100. The signal re-distribution layer includes an array of attachment points where solder ball 72 may be formed and interconnected to vias 53 by conductors 61 of the signal re-distribution layer. The attachment points may be formed as other types of attachments means such as TAB bumps, gold bumps, gold studs, or Ni/Au bumps instead of solder balls 72.

In view of all of the above, it is evident that a novel device and method is disclosed. Included, among other features, is forming a metal shield layer between the signal re-distribution layer and the underlying signal interconnect layers. The metal shield layer terminates the electric field of the undesired noise signals and substantially prevents the noise from affecting the electrical signals formed by the semiconductor devices formed in or on the semiconductor substrate.

For clarity of the explanation, the preferred embodiment is explained, however, metal shield layer 44 should provide the desired shielding for other embodiments in addition to the preferred embodiment. For example, the signal re-distribution layer may have a variety of connector or attachments embodiments. Additionally, the preferred embodiment of a medical device is used to explain the inventions however, the invention may be used in any semiconductor device.

The invention claimed is:

1. A method of forming a shielded semiconductor device comprising:
   providing a semiconductor substrate;
   forming active semiconductor devices on a surface of the semiconductor substrate;
   forming a plurality of conductor layers overlying at least a portion of the active semiconductor devices wherein the plurality of conductor layers interconnect at least a portion of the active semiconductor devices and wherein at least one inter-layer dielectric is interposed between the portion of the active semiconductor devices and the plurality of conductor layers wherein the inter-layer dielectric overlies the surface of the semiconductor substrate;
   forming a metal shield layer overlying the plurality of conductor layers;
   forming a passivation layer used to protect the shielded semiconductor device from contaminants overlying the inter-layer dielectric and underlying the metal shield layer wherein the metal shield layer is separated from the plurality of conductor layers by the passivation layer and wherein the metal shield layer is not coupled to electrical signals or electrical potentials distributed among the active semiconductor.

2. The method of claim 1 wherein forming the passivation layer includes forming the passivation layer with a thickness that is greater than a thickness of the inter-layer dielectric.

3. The method of claim 2 further including forming a second dielectric layer overlying the metal shield layer; and
   forming a conductor re-distribution layer on the second dielectric layer.

4. The method of claim 1 wherein forming the metal shield layer includes forming the passivation layer with a thickness of about two to fifteen microns.

5. The method of claim 1 wherein forming the passivation layer includes forming the passivation layer to include silicon nitride.

6. The method of claim 1 wherein forming the plurality of conductor layers includes forming each conductor layer of the plurality of conductor layers to have a conductor having a width, and
   wherein forming the metal shield layer includes forming a metal on the surface of the passivation layer and patterning the metal to form a plurality of metal regions that have a width that is greater than the width of the conductor of the plurality of conductor layers.

7. The method of claim 1 further including forming the metal shield layer from copper.

8. A method of forming a semiconductor device comprising:
   forming the semiconductor device to include a plurality of conductor layers that interconnect electrical signals between active regions of semiconductor elements of the semiconductor device wherein at least a portion of the plurality of conductor layers overlie at least a portion of the active regions and are separated from the active regions by at least one inter-layer dielectric that is formed with a first thickness;
   forming a metal shield layer overlying the plurality of conductor layers wherein the metal shield layer is separated from the plurality of conductor layers by a passivation layer used to protect the semiconductor device from contaminants overlying the plurality of interconnect layers and underlying the metal shield layer and wherein the metal shield layer does not distribute electrical signals or electrical potentials to the active regions including forming the metal shield layer with a thickness that is greater than the first thickness of the inter-layer dielectric; and
   forming a second dielectric layer overlying the metal shield layer.

9. The method of claim 8 wherein forming the passivation layer includes forming the passivation layer to include a layer of silicon nitride.

10. The method of claim 8 further including forming a signal re-distribution layer overlying the metal shield layer.

11. A method of forming a semiconductor device comprising:
   forming the semiconductor device to include a plurality of conductor layers that interconnect electrical signals between semiconductor elements of the semiconductor device wherein the plurality of conductor layers are separated by at least one inter-layer dielectric that is formed with a first thickness;
   forming a metal shield layer overlying the plurality of conductor layers wherein the metal shield layer is separated from the plurality of conductor layers by a first dielectric layer including forming the metal shield layer with a thickness that is greater than the first thickness of the inter-layer dielectric;
   forming a second dielectric layer overlying the metal shield layer;
   forming an antenna on the second dielectric layer; and
   forming a coaxial connector base on the second dielectric layer wherein a material of the antenna is different from a material of the coaxial connector base.

* * * * *

UNITED STATES PATENT AND TRADEMARK OFFICE
CERTIFICATE OF CORRECTION

PATENT NO. : 8,129,266 B2  
APPLICATION NO. : 12/170202  
DATED : March 6, 2012  
INVENTOR(S) : Hormazdyar M. Dalal et al.

Page 1 of 1

It is certified that error appears in the above-identified patent and that said Letters Patent is hereby corrected as shown below:

Cover Page, at (73), correct 'Componenets' in the assignee name to read Components:

(73) Assignee: SEMICONDUCTOR COMPONENTS INDUSTRIES, LLC

Signed and Sealed this
First Day of May, 2012

David J. Kappos
*Director of the United States Patent and Trademark Office*